(12) United States Patent
Somei et al.

(10) Patent No.: US 7,872,040 B2
(45) Date of Patent: Jan. 18, 2011

(54) RECEPTOR BLOCKER AND VASODILATOR COMPRISING INDOLE DERIVATIVE AS ACTIVE INGREDIENT

(76) Inventors: Masanori Somei, 40-3, Ni, Sodanimachi, Hakusan-shi, Ishikawa (JP) 920-2101; Koki Shigenobu, c/o Toho University, 5-21-16, Omorinishi, Ota-lu, Tokyo (JP) 143-8540; Yoshio Tanaka, c/o The Toho University, 5-21-16, Omorinishi, Ota-ku, Tokyo (JP) 143-8540

( * ) Notice: Subject to any disclaimer, the term of this patent is extended or adjusted under 35 U.S.C. 154(b) by 58 days.

(21) Appl. No.: 11/663,748

(22) PCT Filed: Sep. 16, 2005

(86) PCT No.: PCT/JP2005/017109
§ 371 (c)(1),
(2), (4) Date: Aug. 23, 2007

(87) PCT Pub. No.: WO2006/035617
PCT Pub. Date: Apr. 6, 2006

(65) Prior Publication Data
US 2009/0005430 A1 Jan. 1, 2009

(30) Foreign Application Priority Data
Sep. 27, 2004 (JP) ............................. 2004-280104

(51) Int. Cl.
*A61K 31/405* (2006.01)
*A61K 31/40* (2006.01)
(52) U.S. Cl. .................. 514/415; 514/419; 514/880; 514/929
(58) Field of Classification Search ................. 514/415, 514/419, 866, 909, 880, 929
See application file for complete search history.

(56) References Cited

U.S. PATENT DOCUMENTS

| | | | |
|---|---|---|---|
| 4,087,444 A | 5/1978 | Flaugh et al. | |
| 4,614,807 A | 9/1986 | Flaugh | |
| 5,272,141 A | 12/1993 | Fraschini et al. | |
| 5,276,051 A | 1/1994 | Lesieur et al. | |
| 5,308,866 A | 5/1994 | Lesieur et al. | |
| 5,380,750 A | 1/1995 | Lesieur et al. | |
| 5,430,029 A | 7/1995 | Fraschini et al. | |
| 5,481,021 A | 1/1996 | Garland et al. | |
| 5,552,428 A | 9/1996 | Fraschini et al. | |
| 6,281,241 B1* | 8/2001 | Elsner ........................ 514/415 | |
| 6,730,707 B2 | 5/2004 | Pintor et al. | |
| 2007/0197629 A1 | 8/2007 | Somei et al. | |

FOREIGN PATENT DOCUMENTS

| | | |
|---|---|---|
| FR | 2242091 | 3/1975 |
| JP | 52-57169 A | 5/1977 |
| JP | 5-155769 A | 6/1993 |
| JP | 6-505497 A | 6/1994 |
| JP | 6-183968 A | 7/1994 |
| JP | 6-199784 A | 7/1994 |
| JP | 6-263635 A | 9/1994 |
| JP | 7-112970 A | 5/1995 |
| JP | 2003-519181 A | 6/2003 |
| JP | 2004-500353 A | 1/2004 |
| WO | WO-9215607 | 9/1992 |
| WO | WO-0139771 A1 | 6/2001 |
| WO | WO-01/49286 | 7/2001 |
| WO | WO-02-071873 A1 | 9/2002 |
| WO | WO-03/068743 A1 | 8/2003 |
| WO | WO-2005/084664 A1 | 9/2005 |

OTHER PUBLICATIONS

Girouard et al., "Vasorelaxant effects of the chronic treatment with melatonin on mesenteric artery and aorta of spontaneously hypertensive rats", Journal of Hypertension, vol. 19, No. 8, pp. 1369-1377 (Aug. 2001).*

Rasmussen et al., "Daily melatonin administration at middle age suppresses male rat visceral fat, plasma leptin, and plasma insulin to youthful levels", Endocrinology, vol. 140, No. 2, pp. 1009-1012 (Feb. 1999).*

(Continued)

*Primary Examiner*—Kevin Weddington
(74) *Attorney, Agent, or Firm*—Birch, Stewart, Kolasch & Birch LLP

(57) ABSTRACT

It is intended to find a compound that is structurally simpler than yohimbine, a pentacyclic condensed heterocyclic compound, and has an effect similar to that of yohimbine.

The present invention relates to a pharmaceutical or food composition for $\alpha_2$ receptor blockage comprising a compound represented by the formula (I) or a pharmaceutically acceptable salt thereof:

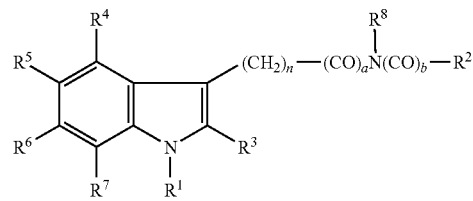

(wherein $R^1$ represents a hydrogen, alkyl group, alkenyl group, alkynyl group, aromatic group, aralkyl group, acyl group, arylsulfonyl group, alkylsulfonyl group, or hydroxyl group; $R^2$ represents a hydrocarbon group; $R^3$, $R^4$, $R^5$, $R^6$, and $R^7$ are the same or different and represent a hydrogen, halogen, alkyl group, or alkoxy group; $R^8$ represents a hydrogen or acyl group; n represents an integer of 1 to 6; and a and b are the same or different and represent 1 or 0).

14 Claims, No Drawings

OTHER PUBLICATIONS

Drago et al., "Acute low doses of melatonin restore full sexual activity in impotent male rats", Brain Research, vol. 878, No. 1-2, pp. 98-104 (Sep. 2000).*

Science Daily (www.sciencedaily.com/releases/2001/02/010215074636). Blood Vessels Hold Key To Thicker Hair Growth (2001).*

Roth, J.A. et al.; J. Biol. Cheml, vol. 274, No. 31, pp. 22041-22047 (1999).

Somei, Masanori et al.; Heterocycles, vol. 53, No. 8, pp. 1725-1736 (2000).

Suzuki, Nobuo et al.; Journal of Pineal Research, vol. 33, pp. 253-258 (2002).

* cited by examiner

RECEPTOR BLOCKER AND VASODILATOR COMPRISING INDOLE DERIVATIVE AS ACTIVE INGREDIENT

TECHNICAL FIELD

The present invention relates to an $\alpha_2$ receptor blocker and a vasodilator comprising an indole derivative as an active ingredient.

BACKGROUND ART $\alpha_2$ receptors include neuronal $\alpha_2$ receptors and non-neuronal $\alpha_2$ receptors. The neuronal $\alpha 2$ receptors are classified into presynaptic $\alpha_2$ receptors and postsynaptic $\alpha 2$ receptors. The former is distributed particularly in peripheral and central noradrenergic nerve terminals and inhibits the release of noradrenalin. Besides, it is also distributed in, for example, cholinergic and serotoninergic nerve terminals and inhibits the release of various types of neurotransmitters. The latter is distributed in, for example, the central nervous system, the sympathetic ganglion, and noradrenergic neuronal dendrites and involved in physiological functions such as hypotensive/bradycardic effects, hyperpolarizing effects, and inhibitory effects on neuronal excitation, respectively. On the other hand, the non-neuronal $\alpha_2$ receptors are distributed in, for example, blood platelets, adipocytes, pancreatic islets of Langerhans, and vascular endothelial cells and involved in physiological functions such as antiplatelet effects, inhibitory effects on lipid degradation, inhibitory effects on insulin secretion, and NO-releasing effects, respectively (Non-Patent Document 1).

Yohimbine or the like is known as an $\alpha_2$ receptor blocking drug known in the art. Yohimbine is indole-based alkaloid contained in the bark of *Pausinystalia yohimbe* (a tree of the family Rubiaceae) or in plants of the genus *Rauwolfia* and is a drug used as an aphrodisiac. Patients with impotence are now sharply increasing due to drugs, geriatric diseases, malignant tumor operations, social environments, mental stresses, and the like. However, a therapy thereof has not been established because the cause of the disease is complicated.

A drug having an $\alpha_2$-receptor antagonistic effect has potential use in many applications such as an aphrodisiac and anti-diabetic drug.

However, yohimbine, which is a pentacyclic condensed heterocyclic compound, is difficult to synthesize due to its complicated structure. Moreover, its complicated structure is a possible cause of side effects.

On the other hand, melatonin (N-acetyl-5-methoxyindole-3-ethaneamine), an indole derivative, represented by the following formula:

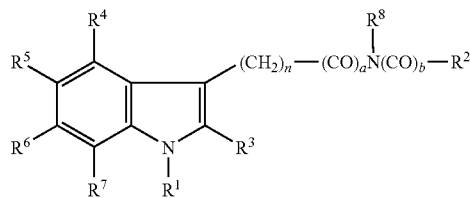

wherein $R^1$ represents a hydrogen atom, $R^2$ represents a methyl group, $R^3$, $R^4$, $R^6$, $R^7$, and $R^8$ represent a hydrogen atom, $R^5$ represents a methoxy group, n represents 2, a represents 0, and b represents 1, has been reported to act in an inhibitory manner on both osteoblasts and osteoclasts (Non-Patent Document 2) and to be effective for female androgenic alopecia and diffuse alopecia (Patent Document 1). Patent Document 2 has disclosed that an indole derivative analogous to melatonin has an intraocular pressure-reducing effect. Alternatively, Patent Document 3 and Non-Patent Document 3 have described a brominated derivative of melatonin, and Non-Patent Document 4 has described various types of 3-substituted indole derivatives.

However, there has been no report that melatonin and indole derivatives analogous to melatonin have an $\alpha_2$-receptor antagonistic effect.

Patent Document 1: JP 2004-500353A
Patent Document 2: U.S. Pat. No. 6,730,707
Patent Document 3: JP 9-511514A
Non-Patent Document 1: I. Muramatsu, Journal of the Japan Pharmaceutical Association, 48 (11), 1987 (1996)
Non-Patent Document 2: N. Suzuki, and A. Hattori, J. Pineal Res., Vol. 33, pp. 253-258 (2002)
Non-Patent Document 3: M. Somei, Y. Fukui, M. Hasegawa, N. Oshikiri, and T. Hayashi, Heterocycles, Vol. 53, pp. 1725-1736 (2000)
Non-Patent Document 4: M. Somei, Recent Advances in the Chemistry of 1-hydroxyindoles, 1-Hydroxytryptophans, and 1-Hydroxytryptamines, Advances in Heterocyclic Chemistry, Vol. 82, ed. by A. R. Katritzky, Elsevier Science (USA), 2002, pp. 101-155

DISCLOSURE OF THE INVENTION

An object of the present invention is to find a compound that is structurally simpler than yohimbine, a pentacyclic condensed heterocyclic compound, and has an effect similar to that of yohimbine.

The present invention encompasses the following inventions:

(1) A pharmaceutical or food composition for $\alpha_2$ receptor blockage comprising a compound represented by the following formula (I) or a pharmaceutically acceptable salt thereof:

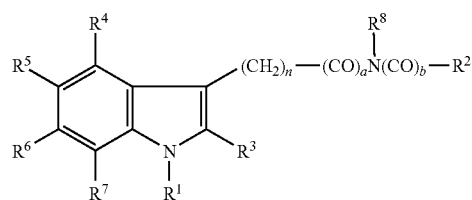

wherein $R^1$ represents a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, or substituted or unsubstituted hydroxyl group; $R^2$ represents a $C_{1-21}$ hydrocarbon group which may be substituted by one or more substituents selected from a $C_{1-6}$ alkyl group, $C_{2-6}$ alkenyl group, $C_{2-6}$ alkynyl group, aromatic group, acyl group, hydroxyl group, carboxyl group, halogen atom, and $C_{1-6}$ alkoxy group; $R^3$, $R^4$, $R^5$, $R^6$, and $R^7$ are the same or different and represent a hydrogen atom, halogen atom, substituted or unsubstituted $C_{1-6}$ alkyl group, or substituted or unsubstituted $C_{1-6}$ alkoxy group; $R^8$ represents a hydrogen atom or substituted or unsubstituted acyl group; n represents an integer of 1 to 6; and a and b are the same or different and represent 1 or 0, except that $R^1$ represents a hydrogen atom, $R^2$ represents a methyl group, $R^3$, $R^4$, $R^6$, $R^7$, and $R^8$ represent a hydrogen atom, $R^5$ represents a methoxy group, n represents 2, a represents 0, and b represents 1.

(2) The composition according to (1), wherein the composition comprises a compound represented by the formula (I) or a pharmaceutically acceptable salt thereof wherein at least one of $R^3$, $R^4$, $R^5$, $R^6$, and $R^7$ is a halogen atom.

(3) The composition according to (1) or (2), wherein the composition comprises a compound represented by the formula (I) or a pharmaceutically acceptable salt thereof wherein $R^3$ is a hydrogen atom, halogen atom, or substituted or unsubstituted $C_{1-6}$ alkoxy group.

(4) The composition according to any of (1) to (3), wherein the composition comprises a compound represented by the formula (I) or a pharmaceutically acceptable salt thereof wherein $R^5$ is a hydrogen atom, substituted or unsubstituted $C_{1-6}$ alkyl group, or substituted or unsubstituted $C_{1-6}$ alkoxy group.

(5) The composition according to any of (1) to (4), wherein the composition comprises a compound represented by the formula (I) or a pharmaceutically acceptable salt thereof wherein $R^2$ is a $C_{4-21}$ aliphatic hydrocarbon group.

(6) The composition according to any of (1) to (4), wherein the composition comprises a compound represented by the formula (I) or a pharmaceutically acceptable salt thereof wherein $R^2$ is a $C_{7-21}$ aliphatic hydrocarbon group.

(7) The composition according to any of (1) to (4), wherein the composition comprises a compound represented by the formula (I) or a pharmaceutically acceptable salt thereof wherein $R^2$ is a bridged cyclic hydrocarbon group.

(8) The composition according to (6), wherein the composition comprises a compound represented by the formula (I) or a pharmaceutically acceptable salt thereof wherein b is 0.

(9) The composition according to any of (1) to (8), wherein the composition comprises a compound represented by the formula (I) or a pharmaceutically acceptable salt thereof wherein n is 3 to 6.

(10) A pharmaceutical or food composition for vasodilation comprising a compound represented by the formula (I) or the pharmaceutically acceptable salt thereof according to any of (1) to (9).

(11) The composition according to (10), wherein the composition exhibits a vasodilatory effect by an $\alpha_2$-receptor antagonistic effect.

(12) A vasodilator comprising melatonin or a pharmaceutically acceptable salt thereof.

The present invention can provide a pharmaceutical or food composition for $\alpha_2$ receptor blockage or for vasodilation using an indole derivative that is structurally simpler than yohimbine and has an effect similar to that of yohimbine.

BEST MODE FOR CARRYING OUT THE INVENTION

Hereinafter, the present invention will be described in detail.

In the present invention, examples of a $C_{1-6}$ alkyl group and "$C_{1-6}$ alkyl" in each substituent include a methyl group, ethyl group, propyl group, isopropyl group, butyl group, isobutyl group, sec-butyl group, tert-butyl group, pentyl group, isopentyl group, hexyl group, cyclopropyl group, cyclobutyl group, cyclopentyl group, and cyclohexyl group.

Examples of a $C_{2-6}$ alkenyl group include a vinyl group, 1-propenyl group, allyl group, 1-butenyl group, 2-butenyl group, pentenyl group, and hexenyl group.

Examples of a $C_{2-6}$ alkynyl group include an ethynyl group, 1-propynyl group, 2-propynyl (propargyl) group, 3-butynyl group, pentynyl group, and hexynyl group.

Examples of an aromatic group include: aromatic hydrocarbon groups such as a phenyl group, tolyl group, and naphthyl group; and aromatic heterocyclic groups such as a furyl group, thienyl group, pyrrolyl group, oxazolyl group, isoxazolyl group, thiazolyl group, isothiazolyl group, imidazolyl group, pyrazolyl group, pyridyl group, pyrimidinyl group, pyridazinyl group, pyrazinyl group, quinolyl group, and isoquinolyl group.

Examples of an aralkyl group include a benzyl group and phenethyl group.

Examples of an acyl group include: $C_{1-6}$ aliphatic acyl groups such as a formyl group, acetyl group, propanoyl group, butanoyl group, pentanoyl group, and hexanoyl group; and aroyl groups such as a benzoyl group and toluoyl group.

Examples of an arylsulfonyl group include: aromatic hydrocarbon-sulfonyl groups such as a benzenesulfonyl group, p-toluenesulfonyl (tosyl) group, and naphthalenesulfonyl group; and aromatic heterocyclic sulfonyl groups such as a furansulfonyl group, thiophenesulfonyl group, pyrrolesulfonyl group, oxazolesulfonyl group, isoxazolesulfonyl group, thiazolesulfonyl group, isothiazolesulfonyl group, imidazolesulfonyl group, pyrazolesulfonyl group, pyridinesulfonyl group, pyrimidinesulfonyl group, pyridazinesulfonyl group, pyrazinesulfonyl group, quinolinesulfonyl group, and isoquinolinesulfonyl group.

Examples of a $C_{1-6}$ alkylsulfonyl group include a methanesulfonyl (mesyl) group and ethanesulfonyl group.

Examples of a $C_{1-21}$ hydrocarbon group include: linear or branched $C_{1-21}$ alkyl groups such as a methyl group, ethyl group, propyl group, isopropyl group, butyl group, isobutyl group, sec-butyl group, tert-butyl group, pentyl group, isopentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group, icosyl group, and henicosyl group; $C_{3-21}$ cycloalkyl groups such as a cyclopropyl group, cyclobutyl group, cyclopentyl group, cyclohexyl group, and cycloheptyl group; $C_{2-21}$ alkenyl groups such as a vinyl group, 1-propenyl group, allyl group, 1-butenyl group, 2-butenyl group, pentenyl group, hexenyl group, and oleyl group; $C_{2-21}$ alkynyl groups such as an ethynyl group, 1-propynyl group, 2-propynyl (propargyl) group, 3-butynyl group, pentynyl group, and hexynyl group; aromatic hydrocarbon groups such as a phenyl group, tolyl group, and naphthyl group; aralkyl groups such as a benzyl group and phenethyl group; bridged cyclic hydrocarbon groups such as an adamantyl group; spirocyclic hydrocarbon groups; and condensed ring hydrocarbon groups.

Examples of a halogen atom include a fluorine atom, chlorine atom, bromine atom, and iodine atom.

Examples of a $C_{1-6}$ alkoxy group include a methoxy group, ethoxy group, propoxy group, isopropoxy group, butoxy group, isobutoxy group, sec-butoxy group, tert-butoxy group, pentyloxy group, isopentyloxy group, hexyloxy group, cyclopropyloxy group, cyclobutyloxy group, cyclopentyloxy group, and cyclohexyloxy group.

A $C_{1-6}$ alkyl group represented by $R^1$, $R^3$, $R^4$, $R^5$, $R^6$, or $R^7$, a $C_{2-6}$ alkenyl group, $C_{2-6}$ alkynyl group, and $C_{1-6}$ alkylsulfonyl group represented by $R^1$, and a $C_{1-6}$ alkoxy group represented by $R^3$, $R^4$, $R^5$, $R^6$, or $R^7$ in the formula (I) may be substituted by one or more substituents selected from an aromatic group, acyl group, hydroxyl group, carboxyl group, halogen atom, $C_{1-6}$ alkoxy group, and so on.

An aromatic group, aralkyl group, acyl group, and arylsulfonyl group represented by $R^1$, a $C_{1-21}$ hydrocarbon group represented by $R^2$, and an acyl group represented by $R^8$ in the formula (I) may be substituted by one or more substituents selected from a $C_{1-6}$ alkyl group, $C_{2-6}$ alkenyl group, $C_{2-6}$ alkynyl group, aromatic group, acyl group, hydroxyl group, carboxyl group, halogen atom, $C_{1-6}$ alkoxy group, and so on.

A hydroxyl group represented by $R^1$ in the formula (I) may be substituted by a substituent selected from a $C_{1-6}$ alkyl group, $C_{2-6}$ alkenyl group, $C_{2-6}$ alkynyl group, aromatic group, aralkyl group, acyl group, and so on. Examples of a hydroxyl group substituted by a $C_{1-6}$ alkyl group include a methoxy group, ethoxy group, propoxy group, isopropoxy group, butoxy group, isobutoxy group, sec-butoxy group, tert-butoxy group, pentyloxy group, isopentyloxy group, hexyloxy group, cyclopropyloxy group, cyclobutyloxy group, cyclopentyloxy group, and cyclohexyloxy group. Examples of a hydroxyl group substituted by a $C_{2-6}$ alkenyl group include a vinyloxy group, 1-propenyloxy group, allyloxy group, 1-butenyloxy group, 2-butenyloxy group, pentenyloxy group, and hexenyloxy group. Examples of a hydroxyl group substituted by a $C_{2-6}$ alkynyl group include an ethynyloxy group, 1-propynyloxy group, and propargyloxy group. Examples of a hydroxyl group substituted by an aromatic group include: aromatic hydrocarbon-oxy groups such as a phenoxy group and naphthyloxy group; and aromatic heterocyclic ring-oxy groups such as a furyloxy group, thienyloxy group, pyrrolyloxy group, oxazolyloxy group, isoxazolyloxy group, thiazolyloxy group, isothiazolyloxy group, imidazolyloxy group, pyrazolyloxy group, pyridyloxy group, pyrimidinyloxy group, pyridazinyloxy group, pyrazinyloxy group, quinolyloxy group, and isoquinolyloxy group. Examples of a hydroxyl group substituted by an aralkyl group include a benzyloxy group and phenethyloxy group. Examples of a hydroxyl group substituted by an acyl group include: $C_{1-6}$ aliphatic acyloxy groups such as a formyloxy group, acetyloxy group, propanoyloxy group, butanoyloxy group, pentanoyloxy group, and hexanoyloxy group; and aroyloxy groups such as a benzoyloxy group and toluoyloxy group.

A compound represented by the formula (I) is preferably a compound wherein at least one of $R^3$, $R^4$, $R^5$, $R^6$, and $R^7$ (particularly, $R^3$, $R^4$, $R^6$, and $R^7$) is a halogen atom, more preferably, two or more of these substituents are halogen atoms, particularly preferably, three or more of these substituents are halogen atoms, in light of an $\alpha_2$-receptor antagonistic effect or vasodilatory effect.

A compound represented by the formula (I) wherein $R^2$ has higher hydrophobicity is more excellent in an $\alpha_2$-receptor antagonistic effect or vasodilatory effect, and a compound wherein $R^2$ is a $C_{4-21}$ aliphatic hydrocarbon group, particularly a $C_{7-21}$ aliphatic hydrocarbon group, for example, a long-chain aliphatic group or bridged cyclic hydrocarbon group (e.g., an adamantyl group) is more preferable than a compound wherein $R^2$ is a methyl group. When $R^2$ is a $C_{7-21}$ aliphatic hydrocarbon group, it is preferred that b should be 0.

In the formula (I), $R^3$ is preferably a hydrogen atom, halogen atom, or substituted or unsubstituted $C_{1-6}$ alkoxy group, and $R^5$ is preferably a hydrogen atom, substituted or unsubstituted $C_{1-6}$ alkyl group, or substituted or unsubstituted $C_{1-6}$ alkoxy group.

When a and b in the formula (I) are 0, it is preferred that n should be 3 to 6.

Examples of a pharmaceutically acceptable salt of the compound represented by the formula (I) include: salts with inorganic acids such as hydrochloric acid, sulfuric acid, phosphoric acid, hydrobromic acid, hydroiodic acid, nitric acid, pyrosulfuric acid, and metaphosphoric acid; and salts with organic acids such as citric acid, benzoic acid, acetic acid, propionic acid, fumaric acid, maleic acid, and sulfonic acid (e.g., methanesulfonic acid, p-toluenesulfonic acid, and naphthalenesulfonic acid). Alternatively, when the compound represented by the formula (I) has a phenolic hydroxyl group or carboxyl group, it can also be used in the form of an alkali metal salt such as a sodium salt and potassium salt.

Of compounds represented by the formula (I), a compound wherein $R^1$ is a hydrogen atom and at least one of $R^3$, $R^4$, $R^5$, $R^6$, and $R^7$ is a halogen atom can be produced, for example, by halogenating a compound represented by the formula (I) wherein at least one of $R^3$, $R^4$, $R^5$, $R^6$, and $R^7$ is a hydrogen atom (e.g., N-acylindole-3-ethaneamines such as melatonin) according to a method described in M. Somei, Y. Fukui, M. Hasegawa, N. Oshikiri, and T. Hayashi, Heterocycles, Vol. 53, pp. 1725-1736 (2000) (Non-Patent Document 3). Alternatively, the compound represented by the formula (I) wherein $R^1$ is a hydrogen atom and at least one of $R^3$, $R^4$, $R^5$, $R^6$, and $R^7$ is a halogen atom can also be produced by halogenating a compound represented by the formula (I) wherein $R^1$ is a hydroxyl group and at least one of $R^3$, $R^4$, $R^5$, $R^6$, and $R^7$ is a hydrogen atom (e.g., N-acyl-1-hydroxyindole-3-ethaneamines such as 1-hydroxymelatonin).

Of compounds represented by the formula (I), a compound wherein $R^1$ is a substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, or substituted or unsubstituted $C_{1-6}$ alkylsulfonyl group can be produced, for example, by reacting a compound represented by the formula (I) wherein $R^1$ is a hydrogen atom (e.g., N-acylindole-3-ethaneamines such as melatonin) with a compound of the formula: $R^1$—X (wherein $R^1$ represents the same as above and X represents a halogen atom) in the presence of a basic catalyst in an organic solvent such as N,N-dimethylfonmamide.

Of compounds represented by the formula (I), a compound wherein $R^1$ is a hydroxyl group can be produced, for example, by treating a compound wherein $R^1$ is a hydrogen atom (e.g., N-acylindole-3-ethaneamines such as melatonin) with sodium boron hydrocyanide in acetic acid or with triethylsilane in trifluoroacetic acid according to a method described in M. Somei, Recent Advances in the Chemistry of 1-Hydroxyindoles, 1-Hydroxytryptophans, and 1-Hydroxytryptamines, Advances in Heterocyclic Chemistry, Vol. 82, ed. by A. R. Katritzky, Elsevier Science (USA), 2002, pp. 101-155 (Non-Patent Document 4) and thereby converting it to a 2,3-dihydroindole derivative, followed by treatment with hydrogen peroxide and sodium tungstate.

Of compounds represented by the formula (I), a compound wherein $R^1$ is a hydroxyl group substituted by a substituent selected from a $C_{1-6}$ alkyl group, $C_{2-6}$ alkenyl group, $C_{2-6}$ alkynyl group, aromatic group, aralkyl group, acyl group, and so on can be produced, for example, by using sodium carbonate, potassium carbonate, triethylamine, pyridine, sodium hydroxide, sodium hydride, butyl lithium, or the like as a base to react a compound wherein $R^1$ is a hydroxyl group with a $C_{1-6}$ alkyl halide, $C_{2-6}$ alkenyl halide, $C_{2-6}$ alkynyl halide, aromatic halide, aralkyl halide, fatty acid halide, fatty acid anhydride, or the like in the coexistence or absence of a metal or transition metal catalyst.

Of compounds represented by the formula (I), a compound wherein a is 0 and b is 1 can be produced by reacting a compound represented by the following formula (II):

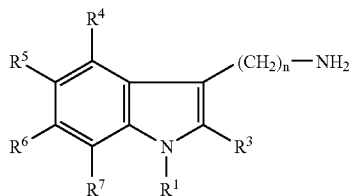

(wherein $R^1$, $R^3$, $R^4$, $R^5$, $R^6$, $R^7$, and n represent the same as above) with an alkanoyl halide or carboxylic acid anhydride or by N-acylating the compound with a carboxylic acid activated with dicyclohexylcarbodiimide or the like.

Of compounds represented by the formula (I), a compound wherein $R^8$ is a substituted or unsubstituted acyl group can be produced, for example, by treating a compound wherein $R^8$ is a hydrogen atom (e.g., N-acylindole-3-ethaneamines such as melatonin) with an acid anhydride such as acetic anhydride.

The product thus obtained may be purified by an approach usually used, for example, column chromatography using silica gel or the like as a carrier or a recrystallization method using methanol, ethanol, chloroform, dimethyl sulfoxide, water, or the like. Examples of an elution solvent in column chromatography include methanol, ethanol, chloroform, acetone, hexane, dichloromethane, ethyl acetate, and mixed solvents thereof.

The compound represented by the formula (I) and the pharmaceutically acceptable salt thereof (hereinafter, referred to as an "indole derivative (I)") have an $\alpha_2$-receptor antagonistic effect and vasodilatory effect. The indole derivative (I) is formulated in pharmaceutical compositions or food compositions such as foods for specified health use and thereby used as a pharmaceutical or food composition for $\alpha_2$ receptor blockage or for vasodilation. For example, it can be utilized as a sexual dysfunction improving drug, anti-obesity drug (lipopenic), hair growth drug, hair regrowth drug, dry mouth improving drug, therapeutic drug for Raynaud's disease, and anti-diabetic drug and has potential use as a "Overall QOL improving drug" targeted for persons in late middle age.

The vasodilatory effect of the pharmaceutical or food composition for vasodilation of the present invention is based on the $\alpha_2$-receptor antagonistic effect and dilates blood vessels without influencing blood pressure. Therefore, the pharmaceutical or food composition for vasodilation is effective for the purpose of dilating cutaneous blood vessels or scalp blood vessels, or further penile blood vessels, and is not used in the treatment of hypertension.

Hereinafter, the dose of the indole derivative (I) and the production of a preparation thereof will be described.

The indole derivative (I) can be administered to animals and humans either directly or together with a pharmaceutical carrier commonly used. Its dosage form is not particularly limited and is appropriately selected as required for use. Examples thereof include: oral preparations such as tablets, capsules, granules, fine granules, powders, sustained-release preparations, suspensions, emulsions, syrups, and elixirs; and parenteral preparations such as injections, suppositories, liniments, and adhesive preparations.

The oral preparations are produced according to a standard method using, for example, starch, lactose, sucrose, mannitol, carboxymethylcellulose, corn starch, and inorganic salts.

In addition to the excipients described above, binders, disintegrators, surfactants, lubricants, fluidity promoters, corrigents, coloring agents, flavors, and so on can be used appropriately in this kind of preparation.

Examples of the binders include starch, dextrin, powdered acacia, gelatin, hydroxypropyl starch, methylcellulose, carboxymethylcellulose sodium, hydroxypropylcellulose, crystalline cellulose, ethylcellulose, polyvinyl pyrrolidone, and macrogol.

Examples of the disintegrators include starch, hydroxypropyl starch, carboxymethylcellulose sodium, carboxymethylcellulose calcium, carboxymethylcellulose, and low-substituted hydroxypropylcellulose.

Examples of the surfactants include sodium lauryl sulfate, soybean lecithin, sucrose fatty acid ester, and polysorbate 80.

Examples of the lubricants include talc, waxes, hydrogenated plant oils, sucrose fatty acid ester, magnesium stearate, calcium stearate, aluminum stearate, and polyethylene glycol.

Examples of the fluidity promoters include light anhydrous silicic acid, dried aluminum hydroxide gel, synthetic aluminum silicate, and magnesium silicate.

The injections are produced according to a standard method, and distilled water for injection, a saline, a glucose aqueous solution, olive oil, sesame oil, peanut oil, soybean oil, corn oil, propylene glycol, polyethylene glycol, or the like can generally be used as a diluent. If necessary, a germicide, antiseptic, and stabilizer may further be added thereto. Moreover, in light of stability, the injections are charged into vials or the like and then frozen, followed by removal of water by a usual freeze-drying technique, and a liquid preparation can be reprepared from the freeze-dried product immediately before use. If necessary, tonicity agents, stabilizers, antiseptics, soothing agents, and so on may be added appropriately.

Examples of the other parenteral preparations include liquid preparations for external use, liniments such as ointments, adhesive preparations, and suppositories for intrarectal administration. They are produced according to a standard method.

The preparation of the present invention may be administered at one to several doses per day to one to several doses per week to month, though the dose differs depending on its dosage form, administration route, and so on.

To exert the intended effect as an oral preparation, an appropriate dose of the preparation in adult is usually 1 to 200 mg in terms of the weight of the indole derivative (I) taken at several doses per day, though the dose differs depending on the age and body weight of a patient and the extent of the disease.

To exert the intended effect as a parenteral preparation, an appropriate dose of the preparation in adult is usually 1 to 50 mg per day in terms of the weight of the indole derivative (I) administered through intravenous injection, intravenous drips, hypodermic injection, or intramuscular injection, though the dose differs depending on the age and body weight of a patient and the extent of the disease.

This description includes part or all of the contents as disclosed in the description of Japanese Patent Application No. 2004-280104, which is a priority document of the present application.

EXAMPLES

Hereinafter, the present invention will be described more specifically with reference to Examples. However, the scope of the present invention is not intended to be limited to these Examples.

Example 1

$\alpha_2$-receptor antagonistic effect and vasodilator effect of indole derivatives (1) Preparation of Blood Vessel Male Wistar rats were euthanized by cervical dislocation under ether anesthesia or without anesthesia and then exsanguinated by cutting the carotid arteries. Immediately thereafter, the thoracic aortae were isolated by thoracotomy. The isolated preparations were held in Krebs-Hepes solutions [mM: NaCl, 126.9; KCl, 5.9; $CaCl_2$, 2.36; $MgCl_2$, 1.18; Hepes, 10.03; glucose, 11.8 (pH=7.4)] gassed with $O_2$ (100%). The connective tissues and adipose tissues were carefully removed under a stereoscopic microscope. Then, the aortic tissue was cut into ring preparations approximately 2 mm in length to use in the experiment. The vascular endothelium was not removed.

(2) Measurement of Muscle Contractile/Relaxant Response

The blood vessel preparations were held in an organ bath (UC-5TD, UFER™ Medical Instrument, Kyoto, Japan) containing 5 ml of Normal Tyrode's solution gassed with 95% $O_2$-5% $CO_2$. Two stainless hooks were used to suspend the preparations. Tension changes were recorded isometrically via tension transducers (T7-8-240, ORIENTEC Co., Ltd, Tokyo, Japan; and TB-611T, NIHON KOHDEN Corp., Tokyo, Japan) and amplifiers (AP-600G and AP-621G, NIHON KOHDEN Corp., Tokyo, Japan; and MSC-2, Labo Support Corporation, Osaka, Japan). Passive tension was set to the optimum tension of 2.0 g. The composition of the Normal Tyrode's solution was as follows: (mM): NaCl, 158.3; KCl, 4.0; $CaCl_2$, 2.0; $MgCl_2$, 1.05; $NaH_2PO_4$, 0.42; $NaHCO_3$, 10.0; glucose, 5.6 (pH=7.4, 37±0.5° C.).

The preparations were then incubated for 60 to 90 minutes in Normal Tyrode's solution, which was replaced with 20-minute to 30-minute intervals. To start the experiment, the preparations were first allowed to contract with a high potassium solution (high-KCl, 80 mM KCl) [composition (mM): NaCl, 82.3; KCl, 80.0; $CaCl_2$, 2.0; $MgCl_2$, 1.05; $NaH_2PO_4$, 0.42; $NaHCO_3$, 10.0; glucose, 5.6 (pH=7.4)] to confirm that the preparations normally contracted. Then, the preparations were washed with a Normal Tyrode's solution, and the experiment was started.

For the purpose of evaluating the potencies of indole derivatives tested, the artery preparations were stimulated with an $\alpha_2$-adrenoceptor agonist clonidine hydrochloride (Wako Pure Chemical Industries, Ltd., Osaka, Japan) ($10^{-7}$ M or $10^{-6}$ M) in the presence of an NO synthase inhibitor $N^G$-nitro-L-arginine methyl ester (DOJNDO Laboratories, Kumamoto, Japan) ($10^{-4}$ M) to thereby induce continuous contraction. After developed tension reached a steady-sate level, samples (indole derivatives) ($10^{-5}$ M) were administered to the bath solution. After the relaxant effects of the samples reached the maximum levels, an $\alpha_2$-adrenoceptor antagonist yohimbine hydrochloride (Wako Pure Chemical Industries, Ltd., Osaka, Japan) ($10^{-5}$ M) was administered to the bath solution. Relaxant response to yohimbine hydrochloride ($10^{-5}$ M) and the height of contraction immediately before sample administration were defined as the maximum relaxation (=100%) and 0%, respectively, and the relaxant effect of the samples were expressed as percentages relative to the maximum relaxation to yohimbine hydrochloride ($10^{-5}$ M).

(3) Drugs Used

The indole derivatives (samples Nos. 1 to 23) were dissolved in 100% dimethyl sulfoxide at a concentration of $10^{-2}$ M just before use and administered to a 5-mL organ bath for evaluation. All the other drugs were dissolved and diluted in distilled water.

(4) Results

The results were expressed as mean±standard error. The results are shown in Table 1

TABLE 1

| Sample No. | Compound name | The number of experiment | Reaction (%) |
| --- | --- | --- | --- |
| 1 | melatonin (N-acetyl-5-methoxyindole-3-ethaneamine) | 3 | 6.7 ± 6.7 |
| 2 | 1-acetylmelatonin (N,1-diacetyl-5-methoxyindole-3-ethaneamine) | 3 | 18.5 ± 9.8 |
| 3 | N-acetylmelatonin (N,N-diacetyl-5-methoxyindole-3-ethaneamine) | 4 | 25.6 ± 7.5 |
| 4 | 4-bromomelatonin (N-acetyl-4-bromo-5-methoxyindole-3-ethaneamine) | 3 | 20.3 ± 4.6 |
| 5 | 2-bromomelatonin (N-acetyl-2-bromo-5-methoxyindole-3-ethaneamine) | 3 | 43.1 ± 16.0 |
| 6 | 2,6-dibromomelatonin (N-acetyl-2,6-dibromo-5-methoxyindole-3-ethaneamine) | 3 | 64.0 ± 4.1 |
| 7 | 2,4-dibromomelatonin (N-acetyl-2,4-dibromo-5-methoxyindole-3-ethaneamine) | 3 | 73.5 ± 15.3 |
| 8 | 2,4,6-tribromomelatonin (N-acetyl-2,4,6-tribromo-5-methoxyindole-3-ethaneamine) | 4 | 85.6 ± 12.0 |
| 9 | 1-acetyl-2,4,6-tribromomelatonin (N,1-diacetyl-2,4,6-tribromo-5-methoxyindole-3-ethaneamine) | 3 | 97.6 ± 2.4 |
| 10 | N-cyclopropylcarbonylindole-3-ethaneamine | 2 | 21.4 |
| 11 | 1-hydroxy-N-cyclopropylcarbonylindole-3-ethaneamine | 4 | 15.7 ± 6.8 |
| 12 | N-pentanoylindole-3-ethaneamine | 6 | 26.9 ± 11.4 |
| 13 | 1-hydroxy-N-pentanoylindole-3-ethaneamine | 3 | 25.6 ± 6.0 |
| 14 | N-heptanoylindole-3-ethaneamine | 3 | 70.0 ± 6.9 |
| 15 | 1-hydroxy-N-heptanoylindole-3-ethaneamine | 4 | 66.2 ± 13.9 |
| 16 | N-nonanoylindole-3-ethaneamine | 3 | 80.7 ± 2.5 |
| 17 | 1-hydroxy-N-nonanoylindole-3-ethaneamine | 4 | 79.0 ± 13 |
| 18 | N-adamantyl-4-(indole-3-yl)butaneamide | 3 | 58.6 ± 10.6 |
| 19 | N-adamantyl-3-(indole-3-yl)propaneamide | 3 | 60.6 ± 20.7 |

TABLE 1-continued

| Sample No. | Compound name | The number of experiment | Reaction (%) |
| --- | --- | --- | --- |
| 20 | N-adamantyl-2-(indole-3-yl)acetamide | 3 | 64.2 ± 8.70 |
| 21 | N-adamantyl-4-(1-hydroxyindole-3-yl)butaneamide | 3 | 87.7 ± 8.53 |
| 22 | N-adamantyl-2-(1-hydroxyindole-3-yl)acetamide | 3 | 100.0 ± 0.00 |
| 23 | N-adamantyl-4-(indole-3-yl)butaneamide | 3 | 91.5 ± 1.32 |

The samples Nos. 1 to 9 were synthesized by a method described in M. Somei, Y. Fukui, M. Hasegawa, N. Oshikiri, and T. Hayashi, Heterocycles, Vol. 53, pp. 1725-1736 (2000) (Non-Patent Document 3). The samples Nos. 10 to 23 were compounds known in the art described in M. Somei, Recent Advances in the Chemistry of 1-Hydroxyindoles, 1-Hydroxytryptophans, and 1-Hydroxytryptamines, Advances in Heterocyclic Chemistry, Vol. 82, ed. by A. R. Katritzky, Elsevier Science (USA), 2002, pp. 101-155 (Non-Patent Document 4) and synthesized by a method described in the document or by a standard method.

All the indole derivatives of the samples Nos. 1 to 23 shown in Table 1 had an $\alpha_2$-receptor antagonistic effect and vasodilatory effect.

All the bromomelatonins (samples Nos. 4 to 9) were shown to have a strong effect as compared with their mother compound melatonin (sample No. 1). Among them, the samples Nos. 6 to 9 were observed to have a strong $\alpha_2$-receptor antagonistic effect and vasodilatory effect comparable at least to those of the $\alpha_2$-adrenoceptor antagonist yohimbine. Furthermore, the strength of the effects was shown to correlate with the number of bromine introduced.

The samples Nos. 14 to 17 were also shown to have a strong vasodilatory effect. Furthermore, the strength of the effect was shown to correlate with the length of a side chain introduced.

The samples Nos. 18 to 23 were also shown to have a strong vasodilatory effect. An adamantyl group was shown to be effective as a fat-soluble functional group.

Thus, bromomelatonins having a long N side chain or an adamantyl group were expected to have the strongest pharmacological effects.

Example 2

Clinical Reports

A test subject was allowed to take the indole derivative (N-nonanoylindole-3-ethaneamine) of the sample No. 16 for 9 months, and followed up.

Test subject: 63-year-old man, healthy, 67 kg in body weight

Information before medication: non-smoking, approximately 180 ml of sake per week, well-balanced diets (meats, vegetables, and fishes) without fatty eating. The test subject has 100% white hair and goes to a barber shop once every five weeks. His mustaches are sparse and remain in an unobtrusive growth state by shaving approximately once every two days. He is in the habit of jogging on Sunday. Muscle ache occurs about two days after the jogging and lasts for approximately 4 days. He feels insecure in erection (ED for approximately half a year).

Dosage and administration: two doses per day, administered at 1 mg around 12 p.m. and at 1 mg around 0 a.m.

Findings: cutaneous blood vessels and penile blood vessels were dilated in approximately 1 to 2 hours after administration, and this dilation lasted for approximately 10 hours.

After one month: black hairs were observed to grow in the scalp of the frontal part of the parietal region that had no hair. The hairs grew approximately 0.5 mm per day. The test subject felt that muscle ache after jogging was slight. Erection was considerably improved. The test subject felt that the degree of memory loss was slight and memory was improved (this may be due to an intracerebral vasodilatory effect).

After three months: the black hairs in the frontal part of the parietal region grew into approximately 1 to 2 cm. Many black hairs were observed to grow throughout the head except for the left frontal part of the temporal region. The whiskers, beards, and vibrissae grew fast, and the test subject felt uncomfortable when the mustaches were not shaved. The nails grew. Only white hairs fell out. Muscle ache after jogging occurred immediately after the activity and disappeared in 2 days. Erection was improved. The test subject felt that memory and retentive powers were recovered.

After nine months: approximately half the hairs in the whole head except for the left frontal part of the temporal region were black hairs. Hair regrowth and growth were favorable. The eyebrows, whiskers, beards, and vibrissae grew well, and shaving was required in the morning and evening. The test subject went to a barber shop once every two weeks. White hairs rapidly fell out when combed, but almost no black hair fell out. Skin tone and complexion were improved. The nails grew fast and were clipped once a week. Muscle ache rapidly disappeared in one day. Erection ability became equal to that in his newly-married days. The test subject became confident not to lose memory and made an attempt to study a foreign language.

The course is under ongoing observation.

All publications, patents, and patent applications cited herein are incorporated herein by reference in their entirety.

INDUSTRIAL APPLICABILITY

The present invention is utilized in pharmaceutical or food fields.

The invention claimed is:

1. A method for blocking $\alpha_2$ receptor comprising administering an effective amount of a compound represented by formula (I) or a pharmaceutically acceptable salt thereof to a subject in need thereof:

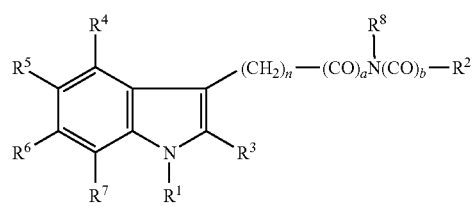

wherein R¹ represents a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, or substituted or unsubstituted hydroxyl group; R² represents a $C_{4-21}$ aliphatic hydrocarbon group which may be substituted by one or more substituents selected from a $C_{1-6}$ alkyl group, $C_{2-6}$ alkenyl group, $C_{2-6}$ alkynyl group, aromatic group, acyl group, hydroxyl group, carboxyl group, halogen atom, and $C_{1-6}$ alkoxy group; R³, R⁴, R⁶, and R⁷ are the same or different and represent a hydrogen atom, halogen atom, substituted or unsubstituted $C_{1-6}$ alkyl group, or substituted or unsubstituted $C_{1-6}$ alkoxy group; R⁵ represents a hydrogen atom; R⁸ represents a hydrogen atom or substituted or unsubstituted acyl group; n represents an integer of 1 to 6; and a and b are the same or different and represent 1 or 0.

2. The method according to claim 1, wherein at least one of R³, R⁴, R⁶, and R⁷ is a halogen atom.

3. The method according to claim 1, wherein R³ is a hydrogen atom, halogen atom, or substituted or unsubstituted $C_{1-6}$ alkoxy group.

4. The method according to claim 1, wherein R² is a $C_{4-21}$ aliphatic hydrocarbon group.

5. The method according to claim 1, wherein R² is a $C_{7-21}$ aliphatic hydrocarbon group.

6. The method according to claim 1, wherein R² is a bridged cyclic hydrocarbon group.

7. The method according to claim 5, wherein b is 0.

8. The method according to claim 1, wherein n is 3 to 6.

9. The method according to claim 1, comprising the further step of dilating blood vessels.

10. The method according to claim 1, wherein the compound represented by formula (I) or a pharmaceutically acceptable salt thereof is contained in a pharmaceutical or food composition.

11. A method for dilating blood vessels comprising administering an effective amount of the compound represented by formula (I) described in claim 1 or a pharmaceutically acceptable salt thereof to a subject in need thereof.

12. A method of treating a patient suffering with a condition affected by the $\alpha_2$ receptor, wherein said condition is sexual dysfunction or hair loss, said method comprising administering a therapeutically effective amount of a compound represented by formula (I) or a pharmaceutically acceptable salt thereof to said patient in need thereof:

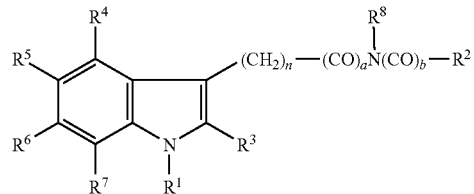

wherein R¹ represents a hydrogen atom, substituted or unsubstituted $C_{1-6}$ alkyl group, substituted or unsubstituted $C_{2-6}$ alkenyl group, substituted or unsubstituted $C_{2-6}$ alkynyl group, substituted or unsubstituted aromatic group, substituted or unsubstituted aralkyl group, substituted or unsubstituted acyl group, substituted or unsubstituted arylsulfonyl group, substituted or unsubstituted $C_{1-6}$ alkylsulfonyl group, or substituted or unsubstituted hydroxyl group; R² represents a $C_{4-21}$ aliphatic hydrocarbon group which may be substituted by one or more substituents selected from a $C_{1-6}$ alkyl group, $C_{2-6}$ alkenyl group, $C_{2-6}$ alkynyl group, aromatic group, acyl group, hydroxyl group, carboxyl group, halogen atom, and $C_{1-6}$ alkoxy group; R³, R⁴, R⁶, and R⁷ are the same or different and represent a hydrogen atom, halogen atom, substituted or unsubstituted $C_{1-6}$ alkyl group, or substituted or unsubstituted $C_{1-6}$ alkoxy group; R⁵ represents a hydrogen atom; R⁸ represents a hydrogen atom or substituted or unsubstituted acyl group; n represents an integer of 1 to 6; and a and b are the same or different and represent 1 or 0.

13. A method according to claim 12, wherein said compound represented by formula (I) or a pharmaceutically acceptable salt thereof is administered in a pharmaceutical carrier selected from the group consisting of tablets, capsules, granules, powders, sustained-release preparations, suspensions, emulsions, syrups, and elixirs.

14. A method according to claim 12, wherein said compound represented by formula (I) or a pharmaceutically acceptable salt thereof is administered orally or parenterally.

* * * * *